United States Patent [19]

Schmidbaur et al.

[11] 4,173,590
[45] Nov. 6, 1979

[54] PROCESS FOR MAKING TETRAMETHYLDIPHOSPHINOMETHANE

[75] Inventors: Hubert Schmidbaur, Garching; Hans-Heinz Karsch, Munich, both of Fed. Rep. of Germany

[73] Assignee: Hoechst Aktiengesellschaft, Fed. Rep. of Germany

[21] Appl. No.: 862,523

[22] Filed: Dec. 20, 1977

[30] Foreign Application Priority Data

Dec. 22, 1976 [DE] Fed. Rep. of Germany ....... 2658127

[51] Int. Cl.² ............................................. C07F 9/50
[52] U.S. Cl. ......................... 260/606.5 P; 260/429 R; 260/429 J; 260/429.9; 260/438.1; 260/438.5 R; 260/439 R
[58] Field of Search ................................ 260/606.5 P

[56] References Cited

U.S. PATENT DOCUMENTS

| | | | |
|---|---|---|---|
| 3,086,053 | 4/1963 | Wagner | 260/606.5 P |
| 3,086,056 | 4/1963 | Wagner | 260/606.5 P |
| 3,370,030 | 2/1968 | Cannelongo | 260/606.5 P X |
| 3,414,624 | 12/1968 | Peterson et al. | 260/606.5 P |
| 3,518,312 | 6/1970 | Maier | 260/606.5 P |

OTHER PUBLICATIONS

Peterson, J. of Organometallic Chem. 8, 199–208 (1967).

*Primary Examiner*—Helen M. S. Sneed
*Attorney, Agent, or Firm*—Connolly and Hutz

[57] ABSTRACT

Novel chemical compounds which comprise tetramethyldiphosphinomethane of the formula:

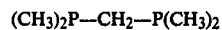

and methyllithium-dimethylphosphine of the formula:

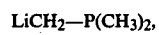

the latter being an intermediate product. Methyllithium-dimethylphosphine is made by reacting a solution of trimethylphosphine with a solution of alkyllithium in an inert solvent with the exclusion of air and moisture, filtering the resulting white precipitate, washing it with the inert solvent, and drying the washed material. Tetramethyldiphosphinomethane is made by reacting, with agitation, a suspension of methyllithium-dimethylphosphine, or dilithiomethane of the formula $Li(CH)_2$ or magnesiomethane of the formula $MgCH_2$ in an organic solvent with dimethylchlorophosphine and distilling the resulting reaction mixture.

4 Claims, No Drawings

PROCESS FOR MAKING TETRAMETHYLDIPHOSPHINOMETHANE

This invention relates to tetramethyldiphosphinomethane of the formula $(CH_3)_2P\text{-}CH_2\text{-}P(CH_3)_2$ and its potential preliminary product, namely methyllithium-dimethylphosphine of the formula $LiCH_2\text{-}P(CH_3)_2$, as novel chemical compounds.

The invention also relates to a process for making methyllithium-dimethylphosphine of the formula $LiCH_2\text{-}P(CH_3)_2$, which comprises: reacting a solution of trimethylphosphine with a solution of alkyllithium in an inert solvent with the exclusion of air and moisture, filtering the resulting white precipitate, washing it with the inert solvent, and drying the washed material.

Further preferred features of the process for making methyllithium-dimethylphosphine provide:

(a) for the inert solvent to comprise aliphatic hydrocarbons, preferably n-hexane, ethers or amines;

(b) for the alkyllithium to comprise secondary or tertiary alkyllithium compounds, preferably tertiary butyllithium, and (c) for the reaction to be effected at temperatures of $-80°$ to $+100°$ C.

The invention also relates to a process for making tetramethyldiphosphinomethane of the formula $(CH_3)_2P\text{-}CH_2\text{-}P(CH_3)_2$, which comprises: reacting, with agitation, a suspension of methyllithium-dimethylphosphine of the formula $LiCH_2\text{-}P(CH_3)_2$ in an organic solvent with dimethylchlorophosphine and distilling the resulting reaction mixture.

The invention finally relates to a process for making tetramethyldiphosphinomethane of the formula $(CH_3)P\text{-}CH_2\text{-}P(CH_3)_2$, which comprises: reacting, with agitation, a suspension of dilithiomethane of the formula $Li_2CH_2$ or magnesiomethane of the formula $MgCH_2$ in an organic solvent with dimethylchlorophosphine and distilling the resulting reaction mixture.

Further preferred features of the two processes for making tetramethyldiphosphinomethane provide:

(a) for the organic solvent to comprise ethers, preferably diethylether or tetrahydrofuran, amines or hydrocarbons, and (b) for the reaction to be effected at temperatures of $-80°$ to $+120°$ C.

In those cases, for example, in which tertiary butyllithium is used as alkyllithium, the various reaction stages of the present process occur, e.g. as shown in the following reaction scheme

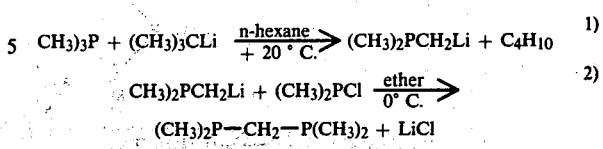

In those cases in which dilithiomethane is used as the starting material, the present process for making tetramethyldiphosphinomethane takes place, e.g. as shown in the following reaction scheme

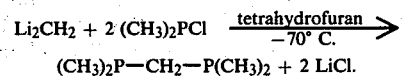

The compound of the formula $(CH_3)_2PCH_2Li$ being a functional derivative of $(CH_3)_3P$ is of general interest for use in syntheses, e.g. inter alia as a complex ligand or for the introduction of the $(CH_3)_2PCH_2$-group into inorganic and organic compounds.

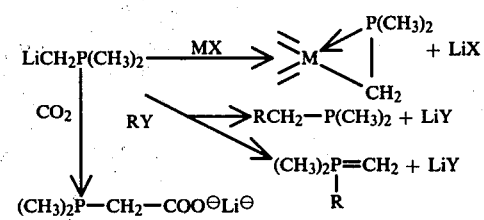

M stands for a transition metal, e.g. Cr. Mn, Fe, Co, Ni; X stands for an anionic group, e.g. a halide, $BF_4^\ominus$, $PF_6^\ominus$; R stands for an organic radical, e.g. alkyl, aryl; Y stands for an electronegative group, e.g. a halide or tosylate.

The compound of the formula $(CH_3)_2P\text{-}CH_2\text{-}P(CH_3)_2$ is an extremely strong ligand for transition metals and a strong nucleophil. Quaternized once or twice, it enables valuable ylides to be obtained substantially more readily than heretofore, as evidenced by the following scheme, in which M stands for a transition metal compound, e.g. a compound of Cr, Mn, Fe, Co, Ni, Cu, Zn and their homologs, and X stands for chlorine, bromine or iodine:

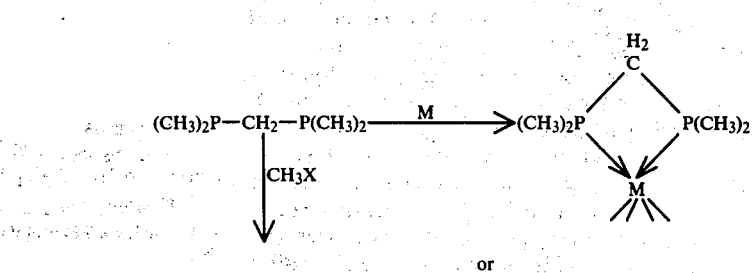

or

-continued

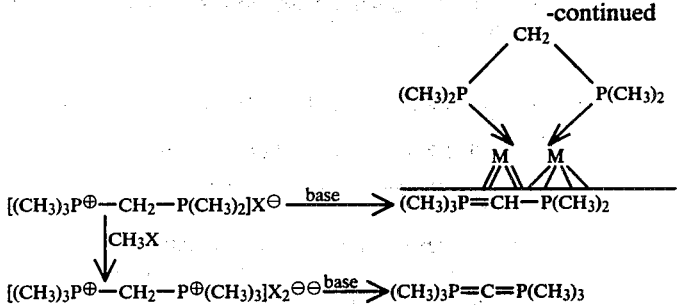

$$[(CH_3)_3P^{\oplus}-CH_2-P(CH_3)_2]X^{\ominus} \xrightarrow{base} (CH_3)_3P=CH-P(CH_3)_2$$

$$\downarrow CH_3X$$

$$[(CH_3)_3P^{\oplus}-CH_2-P^{\oplus}(CH_3)_3]X_2{}^{\ominus\ominus} \xrightarrow{base} (CH_3)_3P=C=P(CH_3)_3$$

In addition to this, the compound of the formula $(CH_3)_2P-CH_2-P(CH_3)_2$ is a substance which provides a key to the synthesis of semi- and double chalcogene compounds which in turn constitute novel complex ligands to obtain altogether up to 15.25 g of the product (93% of the theoretical).

The white mass was soluble in tetrahydrofuran and extremely reactive towards $H_2O$, $CO_2$, $O_2$, $CS_2$, metal halides, acids, oxidation agents, and functional organic

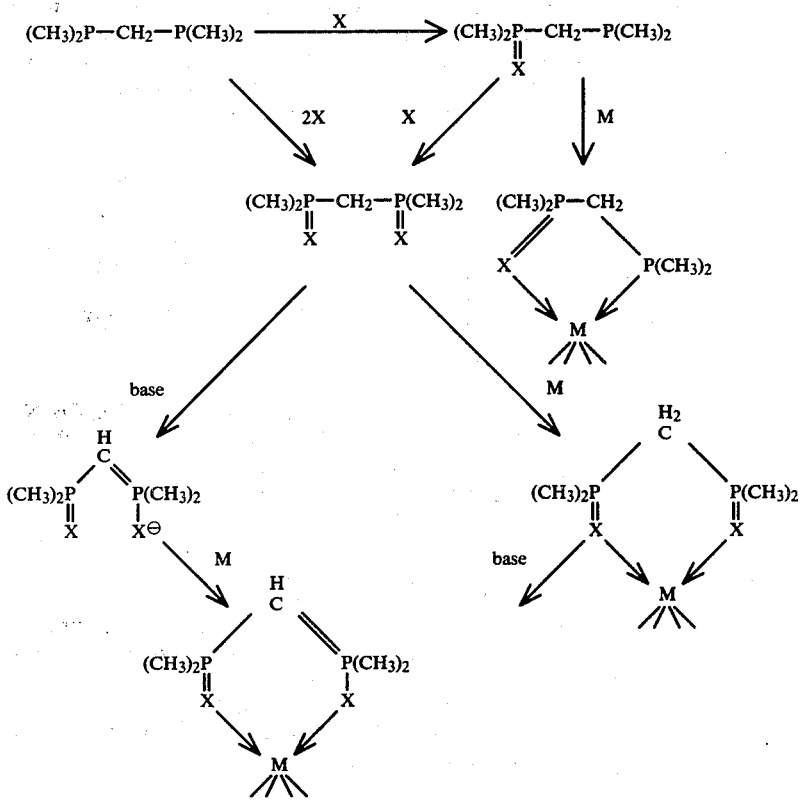

in which X stands for a chalcogene, e.g. O, S, Se and M stands for a metal (compound) of the main and subgroups.

EXAMPLE 1

(Preparation of LiCH$_2$-P(CH$_3$)$_2$)

15.2 g (200 millimols) of trimethylphosphine was added under dry nitrogen as an inert protective gas and at room temperature to 100 ml of a 2-molar solution of tertiary butyllithium (12.8 g =200 millimols) in hexane. A white precipitate of methyllithium-dimethylphosphine was found to have been formed within 8 hours. It was filtered off, washed with n-hexane and dried under vacuum (12.3 g =150 millimols =75% of the theoretical). The residual solution was allowed to stand for some prolonged time (up to 5 days with gentle heating, if necessary or desirable) and precipitate was occasionally removed therefrom. In this manner, it was possible compounds.

NMR-spectra: $^1$H-NMR: $\delta CH_3$ 1.32, d. J(HCP)1.35: $\delta CH_2$-0.40, d. J(HCP) 0.75: $^{31}$P-NMR: $\delta P$-−51.6.

Elementary analysis: C$_3$H$_8$LiP (82.0): Calculated: C 43.94, H 9.84 weight %: Found: C 44.88, H 9.82 weight %.

EXAMPLE 2

(Preparation of (CH$_3$)$_2$P-CH$_2$-P(CH$_3$)$_2$) 10.0 g (122 millimols) of methyllithium-dimethylphosphine of Example 1 was suspended in 100 ml of diethylether. The suspension was agitated and cooled with ice and admixed dropwise at 0° C. within 30 minutes with a solution of 9.5 ml of dimethylchlorophosphine (120.8 millimols) in 40 ml of diethylether.

The whole was agitated for a further 2 hours, filtered and the filtrate was distilled. 10.7 g of a colorless reactive liquid distilled over at a boiling point of 42° C. under 12 mm Hg.

The melting point was at −59° to −56° C.

The liquid underwent spontaneous and partially vigorous reaction with: O$_2$, S$_8$, CS$_2$, metals and metal compounds, organic halogen compounds, and acids. The yield of tetramethyldiphosphinomethane was 65% of the theoretical.

NMR-spectra: $^1$H-NMR: δCH$_3$ 1.18, t', N =2.9 (A$_6$XX'A$_6$'). {$^{31}$P}: s. δCH$_2$ 1.40, t, J(HCP) 0.9 {$^{31}$P}:s. $^{31}$P-NMR: δP −55.7.

Elementary analysis: C$_5$H$_{14}$P$_2$ (136.1): Calculated: C 44.12, H 10.37 weight %: Found: C 44.07, H 10.19 weight %:

EXAMPLE 3

(Preparation of (CH$_3$)$_2$P-CH$_2$-P(CH$_3$)$_2$) 2.8 g (0.1 mol) of dilithiomethane was suspended in 50 ml of tetrahydrofuran and the suspension was cooled to −70° C.

Next, the suspension was admixed dropwise with agatition with 19.3 g (0.2 mol) of dimethylchlorophosphine. While agitation was continued, the whole was allowed to get warm, and agitation was continued for a further 1 hour. The resulting solution was filtered. The filtrate was fractionated. 10.6 g of a colorless liquid distilled over at 42° C./10 mm Hg. Tetramethyldiphosphinomethane was obtained in a yield of 78% of the theoretical.

We claim:

1. A process of making tetramethyldiphosphinomethane of the formula (CH$_3$)$_2$P-CH$_2$-P(CH$_3$)$_2$, which comprises: reacting, with agitation, a suspension of dilithiomethane of the formula Li$_2$CH$_2$ or magnesiomethane of the formula MgCH$_2$ in an organic solvent with dimethylchlorophosphine and distilling the resulting reaction mixture.

2. A process as claimed in claim 1, wherein the organic solvent is an ether, an amine or a hydrocarbon.

3. A process as claimed in claim 1, wherein the reaction is effected at temperatures of −80° to 120° C.

4. A process as claimed in claim 2, wherein the reaction is effected at temperatures of −80° to 120° C.

* * * * *